US011578026B2

(12) United States Patent
Dennis-Smither et al.

(10) Patent No.: US 11,578,026 B2
(45) Date of Patent: Feb. 14, 2023

(54) PROCESS FOR DEHYDRATING ALCOHOLS TO ETHERS

(71) Applicant: BP P.L.C., London (GB)

(72) Inventors: Benjamin James Dennis-Smither, Hull (GB); John Glenn Sunley, Hull (GB); Fiona Jackson, Hull (GB)

(73) Assignee: BP P.L.C., London (GB)

( * ) Notice: Subject to any disclaimer, the term of this patent is extended or adjusted under 35 U.S.C. 154(b) by 0 days.

(21) Appl. No.: 17/433,122

(22) PCT Filed: Feb. 14, 2020

(86) PCT No.: PCT/EP2020/053868
§ 371 (c)(1),
(2) Date: Aug. 23, 2021

(87) PCT Pub. No.: WO2020/169466
PCT Pub. Date: Aug. 27, 2020

(65) Prior Publication Data
US 2022/0144739 A1    May 12, 2022

(30) Foreign Application Priority Data
Feb. 22, 2019  (EP) ..................... 19158741

(51) Int. Cl.
*C07C 41/09*     (2006.01)
(52) U.S. Cl.
CPC .................. *C07C 41/09* (2013.01)

(58) Field of Classification Search
CPC ........................................ C07C 41/09
See application file for complete search history.

(56) References Cited

U.S. PATENT DOCUMENTS

2012/0220804 A1    8/2012  Mitschke et al.
2014/0275636 A1 *  9/2014  Zhang ................. C07C 41/09
                                                 568/698

FOREIGN PATENT DOCUMENTS

FR     2998567 A1 *  5/2014  ............... C07C 1/24
WO     97/35823 A1    10/1997

OTHER PUBLICATIONS

International Search Report and Written Opinion of the International Searching Authority for International Application No. PCT/EP2020/053868, completed Apr. 28, 2020.

* cited by examiner

*Primary Examiner* — Rosalynd A Keys
(74) *Attorney, Agent, or Firm* — McDonnell Boehnen Hulbert & Berghoff LLP

(57) ABSTRACT

A process for dehydrating $C_2+$ alcohols to ether products in the presence of a catalyst and promoter, wherein the catalyst is at least one aluminosilicate zeolite catalyst which is a medium pore zeolite having a 3-dimensional framework structure, and the promoter is one or more organic carbonyl compounds or derivatives thereof, and wherein and the molar ratio of promoter to $C_2+$ alcohols is maintained at less than 1.

15 Claims, No Drawings

PROCESS FOR DEHYDRATING ALCOHOLS TO ETHERS

This application is a national stage application under 35 U.S.C. § 371 of International Application No. PCT/EP2020/053868, filed Feb. 14, 2020, which claims priority to European Patent Application No. 19158741.9, filed Feb. 22, 2019, the disclosures of which are explicitly incorporated by reference herein.

This invention relates in general to a dehydration process and in particular to a process for the dehydration of alcohols to prepare ethers in the presence of an aluminosilicate zeolite catalyst and a promoter compound.

Ethers are widely used chemicals and are produced on an industrial scale around the world. Processes for the preparation of ethers are known in the art; for example, the preparation of ethers by dehydration of alcohols using a solid acid catalyst are known in the art, for example the use of zeolites, such as ZSM-5, for the dehydration of methanol to dimethyl ether or the dehydration of ethanol to diethyl ether is known in the art.

Applicant has now found that organic carbonyl compounds or derivatives thereof, in particularly compounds which are selected from:
(i) aldehydes of formula $R^{A1}CHO$(Formula I), $R^{A1}CHO$, wherein $R^{A1}$ is hydrogen, a $C_1$-$C_{11}$ alkyl group, a $C_3$-$C_{11}$ alkyl group in which 3 or more carbon atoms are joined to form a ring, or an optionally substituted aromatic group;
(ii) acetal derivatives of an aldehyde of Formula I;
(iii) ketones of formula $R^{K1}COR^{K2}$ (Formula II), wherein $R^{K1}$ and $R^{K2}$ are identical or different and each is a $C_1$-$C_{11}$ alkyl group, a $C_3$-$C_{11}$ alkyl group in which 3 or more carbon atoms are joined to form a ring, or an optionally substituted aromatic group, and furthermore $R^{K1}$ and $R^{K2}$ together with the carbonyl carbon atom to which they are bonded may form a cyclic ketone;
(iv) ketal derivatives of ketones of Formula II;
(v) esters of formula $R^{E1}CO_2R^{E2}$ (Formula III), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group; and,
(vi) di-esters of formula $R^{E1}(CO_2R^{E2})_2$ (Formula IV), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group,
have a beneficial effect on the rate of dehydration of $C_2$+ alcohols which are carried out in the presence of an aluminosilicate zeolite catalyst which is a medium pore zeolite having a 3-dimensional framework structure.

Accordingly, the present invention provides a process for dehydrating $C_2$+ alcohols to ether products in the presence of a catalyst and promoter, wherein the catalyst is at least one aluminosilicate zeolite catalyst which is a medium pore zeolite having a 3-dimensional framework structure, and the promoter is one or more organic carbonyl compounds or derivatives thereof, wherein and the molar ratio of promoter to $C_2$+ alcohols is maintained at less than 1.

According to a particular embodiment, the present invention provides a process for dehydrating $C_2$+ alcohols to ether products in the presence of a catalyst and promoter, wherein the catalyst is at least one aluminosilicate zeolite catalyst which is a medium pore zeolite having a 3-dimensional framework structure, and the promoter is one or more compounds selected from:
(i) an aldehyde of formula $R^{A1}CHO$(Formula I), $R^{A1}CHO$, wherein $R^{A1}$ is hydrogen, a $C_1$-$C_{11}$ alkyl group, a $C_3$-$C_{11}$ alkyl group in which 3 or more carbon atoms are joined to form a ring, or an optionally substituted aromatic group;
(ii) an acetal derivative of an aldehyde of Formula I;
(iii) a ketone of formula $R^{K1}COR^{K2}$ (Formula II), wherein $R^{K1}$ and $R^{K2}$ are identical or different and each is a $C_1$-$C_{11}$ alkyl group, a $C_3$-$C_{11}$ alkyl group in which 3 or more carbon atoms are joined to form a ring, or an optionally substituted aromatic group, and furthermore $R^{K1}$ and $R^{K2}$ together with the carbonyl carbon atom to which they are bonded may form a cyclic ketone;
(iv) a ketal derivative of a ketone of Formula II;
(v) an ester of formula $R^{E1}CO_2R^{E2}$ (Formula III), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group; and,
(vi) a di-ester of formula $R^{E1}(CO_2R^{E2})$ (Formula IV), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group,
and wherein and the molar ratio of promoter to $C_2$+ alcohols is maintained at less than 1.

Advantageously, the promoters of the present invention allow productivity to ether products to be improved in dehydration reactions of $C_2$+ alcohols which are carried out in the presence of aluminosilicate zeolite catalysts which are medium pore zeolites having a 3-dimensional framework structure.

Also, according to the present invention there is provided a method of improving the productivity to ether products in a process for dehydrating $C_2$+ alcohols in the presence of a catalyst and a promoter, wherein the catalyst is at least one aluminosilicate zeolite catalyst which is a medium pore zeolite having a 3-dimensional framework structure, and the promoter is one or more organic carbonyl compounds or derivatives thereof, and wherein and the molar ratio of promoter to $C_2$+ alcohols is maintained at less than 1.

According to a particular embodiment of the present invention, there is provided a method of improving the productivity to ether products in a process for dehydrating $C_2$+ alcohols in the presence of a catalyst and a promoter, wherein the catalyst is at least one aluminosilicate zeolite catalyst which is a medium pore zeolite having a 3-dimensional framework structure, and the promoter is one or more compounds selected from:
(i) an aldehyde of formula $R^{A1}CHO$(Formula I), $R^{A1}CHO$, wherein $R^{A1}$ is hydrogen, a $C_1$-$C_{11}$ alkyl group, a $C_3$-$C_{11}$ alkyl group in which 3 or more carbon atoms are joined to form a ring, or an optionally substituted aromatic group;
(ii) an acetal derivative of an aldehyde of Formula I;
(iii) a ketone of formula $R^{K1}COR^{K2}$ (Formula II), wherein $R^{K1}$ and $R^{K2}$ are identical or different and each is a $C_1$-$C_{11}$ alkyl group, a $C_3$-$C_{11}$ alkyl group in which 3 or more carbon atoms are joined to form a ring, or an optionally substituted aromatic group, and furthermore $R^{K1}$ and $R^{K2}$ together with the carbonyl carbon atom to which they are bonded may form a cyclic ketone;
(iv) a ketal derivative of a ketone of Formula II;
(v) an ester of formula $R^{E1}CO_2R^{E2}$ (Formula III), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group; and, (vi) a di-ester of formula $R^{E1}(CO_2R^{E2})_2$ (Formula IV), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group, and wherein and the molar ratio of promoter to $C_2+$ alcohols is maintained at less than 1.

Yet further according to the present invention there is provided the use of a promoter in a process for the catalytic dehydration of $C_2+$ alcohols to ether products to improve productivity to ether products, wherein the catalyst is at least one aluminosilicate zeolite catalyst which is a medium pore zeolite having a 3-dimensional framework structure, and the promoter is one or more organic carbonyl compounds or derivatives thereof, and wherein and the molar ratio of promoter to $C_2+$ alcohols is maintained at less than 1.

Yet further according to a particular embodiment of the present invention there is provided the use of a promoter in a process for the catalytic dehydration of $C_2+$ alcohols to ether products to improve productivity to ether products, wherein the catalyst is at least one aluminosilicate zeolite catalyst which is a medium pore zeolite having a 3-dimensional framework structure, and the promoter is one or more compounds selected from:

(i) an aldehyde of formula $R^{A1}CHO$(Formula I), $R^{A1}CHO$, wherein $R^{A1}$ is hydrogen, a $C_1$-$C_{11}$ alkyl group, a $C_3$-$C_{11}$ alkyl group in which 3 or more carbon atoms are joined to form a ring, or an optionally substituted aromatic group;

(ii) an acetal derivative of an aldehyde of Formula I;

(iii) a ketone of formula $R^{K1}COR^{K2}$ (Formula II), wherein $R^{K1}$ and $R^{K2}$ are identical or different and each is a $C_1$-$C_{11}$ alkyl group, a $C_3$-$C_{11}$ alkyl group in which 3 or more carbon atoms are joined to form a ring, or an optionally substituted aromatic group, and furthermore $R^{K1}$ and $R^{K2}$ together with the carbonyl carbon atom to which they are bonded may form a cyclic ketone;

(iv) a ketal derivative of a ketone of Formula II;

(v) an ester of formula $R^{E1}CO_2R^{E2}$ (Formula III), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group; and, (vi) a di-ester of formula $R^{E1}(CO_2R^{E2})_2$ (Formula IV), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group, and wherein and the molar ratio of promoter to $C_2+$ alcohols is maintained at less than 1.

A further aspect of the present invention provides a process for dehydrating $C_2+$ alcohols to ether products in the presence of a catalyst, wherein the catalyst is at least one aluminosilicate zeolite catalyst which is a medium pore zeolite having a 3-dimensional framework structure, and wherein prior to using the catalyst in the dehydration process, the catalyst has been impregnated with a promoter which is an organic carbonyl compound or derivative thereof.

According to a particular aspect of the present invention, there is provided a process for dehydrating $C_2+$ alcohols to ether products in the presence of a catalyst, wherein the catalyst is at least one aluminosilicate zeolite catalyst which is a medium pore zeolite having a 3-dimensional framework structure, and wherein prior to using the catalyst in the dehydration process, the catalyst has been impregnated with a promoter selected from:

(i) an aldehyde of formula $R^{A1}CHO$(Formula I), $R^{A1}CHO$, wherein $R^{A1}$ is hydrogen, a $C_1$-$C_{11}$ alkyl group, a $C_3$-$C_{11}$ alkyl group in which 3 or more carbon atoms are joined to form a ring, or an optionally substituted aromatic group;

(ii) an acetal derivative of an aldehyde of Formula I;

(iii) a ketone of formula $R^{K1}COR^{K2}$ (Formula II), wherein $R^{K1}$ and $R^{K2}$ are identical or different and each is a $C_1$-$C_{11}$ alkyl group, a $C_3$-$C_{11}$ alkyl group in which 3 or more carbon atoms are joined to form a ring, or an optionally substituted aromatic group, and furthermore $R^{K1}$ and $R^{K2}$ together with the carbonyl carbon atom to which they are bonded may form a cyclic ketone;

(iv) a ketal derivative of a ketone of Formula II;

(v) an ester of formula $R^{E1}CO_2R^{E2}$ (Formula III), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group; and, (vi) a di-ester of formula $R^{E1}(CO_2R^{E2})_2$ (Formula IV), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group.

The catalytic dehydration reaction of an alcohol to an ether can be represented by the following equation: $R^xOH + R^yOH \leftrightarrows R^xOR^y + water$, wherein $R^x$ and $R^y$ may be the same or different.

In the present invention, the $C_2+$ alcohols to be dehydrated may be any $C_2+$ alcohol which is capable of being of forming an ether through dehydration. In some or all embodiments, the $C_2+$ alcohols are monohydric $C_2+$ alcohols. Typically, the $C_2+$ alcohols are primary alcohols.

In some or all embodiments, the $C_2+$ alcohols are $C_2$ to $C_{12}$ alcohols, preferably $C_2$ to $C_{12}$ monohydric alcohols.

In some or all embodiments of the present invention, the $C_2+$ alcohols only comprise an unsubstituted hydrocarbyl and a hydroxyl group, preferably the $C_2+$ alcohols comprise an unsubstituted $C_2$ to $C_{12}$ hydrocarbyl group and a hydroxyl group.

The $C_2$ to $C_{12}$ hydrocarbyl group may be any suitable saturated or unsaturated, linear, branched, or cyclic hydrocarbyl group comprising from 2 to 12 carbon atoms, preferably from 2 to 10 carbon atoms, more preferably from 2 to 8 carbon, such as from 2 to 6 carbon atoms. In some or all embodiments, the $C_2+$ alcohols comprise a $C_2$ to $C_6$ alkyl group and a hydroxyl group.

In some or all embodiments, the $C_2+$ alcohols to be dehydrated are primary alcohols comprising a $C_2$ to $C_6$ alkyl group and a hydroxyl group, such as, for example, one or more alcohols selected from the group comprising ethanol, n-propanol, iso-propanol, n-butanol, iso-butanol, and tert-butanol. In some or all embodiments, the $C_2+$ alcohols to be dehydrated are primary alcohols comprising a linear $C_2$ to $C_6$ alkyl group and a hydroxyl group, for example, one or more alcohols selected from the group comprising ethanol, n-propanol, and n-butanol.

The $C_2+$ alcohols to be dehydrated may be a single $C_2+$ alcohol species or may be a mixture of two or more $C_2+$ alcohol species. In some or all embodiments of the present invention, the $C_2+$ alcohols to be dehydrated is a single $C_2+$ alcohol species.

In the present invention, the dehydration process is carried out in the presence of at least one aluminosilicate zeolite catalyst which is a medium pore zeolite having a 3-dimensional framework structure.

Aluminosilicate zeolites are crystalline microporous materials which have framework structures constructed from tetrahedra of $SiO_4$ and $AlO_4$ that share vertices. Such tetrahedral species are generally referred to as $TO_4$ species wherein the T atom is silicon or aluminium. Aluminium 'T' atoms can be partially or wholly replaced by one or more gallium, boron or iron atoms. For the purposes of the present invention, such gallium, boron or iron modified zeolites are considered to fall within the definition of the term 'aluminosilicate zeolites'.

Silicoaluminophosphate structures containing $PO_4$ tetrahedra are not considered to be aluminosilicate materials and consequently, such silicoaluminophosphates, for example SAPO-type materials, are not within the scope of the present invention.

A zeolite framework topology contains a regular array of pores, channels and/or pockets that vary in size, shape and dimensionality. These framework topologies or structure types of zeolites are assigned three-letter structure codes by the Structure Commission of the International Zeolite Association, under the authority of IUPAC.

A description of zeolites, their framework codes, structure, dimensionality, properties and methods of synthesis can be found in The *Atlas of Zeolite Framework Types* (C. Baerlocher, W. M. Meier, D. H. Olson, 5$^{th}$ Ed. Elsevier, Amsterdam, 2001) in conjunction with the web-based version (http://www.iza-structure.org/databases/).

Zeolite crystals contain pore or channel systems of molecular dimensions with fixed geometry and size and can be classified according to the number of channels running in different directions within the zeolite framework structure. A zeolite is described as 1-dimensional, 2-dimensional or 3-dimensional if the zeolite has one, two or three channels in different directions, respectively.

Zeolites may also be classified according to the size of their pores. Zeolite channels with pore openings limited by 8 T atoms in tetrahedral co-ordination are defined as having an 8-membered ring, zeolite channels with pore openings limited by 10 T atoms in tetrahedral co-ordination are defined as having a 10-membered ring, and zeolite channels with pore openings limited by 8 T atoms in tetrahedral co-ordination are defined as having a 12-membered ring. Zeolites can also conveniently be classified based upon the channel containing the largest pore opening, and zeolites with the largest pore openings limited by 8 T atoms in tetrahedral co-ordination (8-membered rings) may be defined as "small pore zeolites" (8-membered rings); zeolites with the largest pore openings limited by 10 T atoms in tetrahedral co-ordination (10-membered rings) may be defined as "medium pore zeolites"; and, zeolites with the largest pore openings limited by 12 T atoms in tetrahedral co-ordination (12-membered rings) may be defined as "large pore zeolites".

Non-limiting examples of small pore zeolites are those of framework types CHA, RHO and KFI.

Non-limiting examples of medium pore zeolites are those of framework types TON, MTT, FER, MWW, MFI, EUO, MEL, MFS, and TER.

Non-limiting examples of large pore zeolites are those of framework types MOR, BEA, FAU, EON, IWV, SEW and USI.

The extent to which the dehydration reaction is promoted may vary depending on factors such as the structure of the zeolite and nature of the promoter employed in the reaction. Desirably, to promote increased productivity, the channels of a zeolite must be of a size such that a promoter is able to diffuse into the zeolite channels.

In some or all embodiments of the present invention, the catalyst comprises at least one aluminosilicate zeolite catalyst which is a medium pore zeolite having a 3-dimensional framework structure. In some or all embodiments of the present invention, the catalyst is at least one aluminosilicate zeolite catalyst which is a medium pore zeolite having a 3-dimensional framework structure.

In some or all embodiments of the present invention, the catalyst is an aluminosilicate zeolite selected from framework types MFI and MEL. Examples of aluminosilicate zeolites of framework type MFI include ZSM-5. Examples of aluminosilicate zeolites of framework type MEL include ZSM-11.

Typically, zeolites are synthesised from synthesis mixtures comprising a silica source, an alumina source, alkali metal hydroxide and water in desired proportions. The synthesis mixture is maintained, with or without agitation, under temperature, pressure and time conditions sufficient to form a crystalline aluminosilicate zeolite. The resulting zeolite contains alkali metal as a cation. Such cations may be replaced by known ion-exchange techniques. For example, the zeolite may be contacted with aqueous solutions of ammonium salts to substitute ammonium ions for the alkali metal cations. Ammonium-form zeolites are also available commercially.

Whilst zeolites in their ammonium-form can be catalytically active, for use in the present invention it is preferred to utilise a zeolite in its hydrogen-form (H-form). H-form zeolites are commercially available. Alternatively, an ammonium-form zeolite can be converted to the H-form by known techniques, for example by calcining the ammonium-form zeolite, in air or inert gas, at high temperature, for example at a temperature of 500° C. or higher.

In some or all embodiments of the present invention, the aluminosilicate zeolite catalyst is a zeolite which is a hydrogen-form (H-form) zeolite.

For use in the present invention, an aluminosilicate zeolite may be composited with at least one binder material. The binder material may be a refractory inorganic oxide, such as silicas, aluminas, alumina-silicates, magnesium silicates, magnesium aluminium silicates, titanias and zirconias.

For use in the present invention, the relative proportions of aluminosilicate zeolite and binder material in the composite may vary widely. Suitably, the binder material can be present in an amount of from 10% to 90% by weight of the composite.

For use in the present invention, the silica to alumina molar ratio of a zeolite may vary widely but suitably is in the range 10 to 300, for example in the range 20 to 280, such as in the range 20 to 100.

The promoter compounds used in the present invention are organic carbonyl compounds or derivatives thereof. In the present invention, the promoter compounds may be used individually, or mixture of any two or more promoter compounds may also be used in the present invention. In some or all embodiments of the present invention, only a single species of promoter compound is used.

In some or all embodiments of the present invention, the promoter compounds for use in the present invention are selected from one or more compounds selected from:

(i) an aldehyde of formula $R^{41}$CHO(Formula I), $R^{41}$CHO, wherein $R^{41}$ is hydrogen, a $C_1$-$C_{11}$ alkyl group, a $C_3$-$C_{11}$ alkyl group in which 3 or more carbon atoms are joined to form a ring, or an optionally substituted aromatic group;

(ii) an acetal derivative of an aldehyde of Formula I;

(iii) a ketone of formula $R^{K1}COR^{K2}$ (Formula II), wherein $R^{K1}$ and $R^{K2}$ are identical or different and each is a $C_1$-$C_{11}$ alkyl group, a $C_3$-$C_{11}$ alkyl group in which 3 or more carbon atoms are joined to form a ring, or an optionally substituted aromatic group, and furthermore $R^{K1}$ and $R^{K2}$ together with the carbonyl carbon atom to which they are bonded may form a cyclic ketone;

(iv) a ketal derivative of a ketone of Formula II;

(v) an ester of formula $R^{E1}CO_2R^{E2}$ (Formula III), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group; and, (vi) a di-ester of formula $R^{E1}(CO_2R^{E2})_2$ (Formula IV), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group.

The promoters of compounds (i) to (vi) may be used individually, or mixture of any two or more promoter compounds may also be used in the present invention. In some or all embodiments of the present invention, only a single species of promoter compound is used.

Promoter compounds for use in the present invention may be selected from (i) aldehydes of Formula I $R^{41}CHO$, wherein $R^{41}$ is hydrogen, a $C_1$-$C_{11}$ alkyl group, a $C_3$-$C_{11}$ alkyl group in which 3 or more carbon atoms are joined to form a ring, or an optionally substituted aromatic group, or (ii) acetal derivatives of the aldehydes of Formula I.

Mixtures of aldehydes of Formula I and their acetal derivatives may also be used in the present invention.

In some or all embodiments of the present invention, $R^{41}$ is hydrogen, a $C_1$-$C_7$ alkyl group, a $C_3$-$C_7$ alkyl group in which 3 or more carbon atoms are joined to form a ring, or an optionally substituted aromatic group.

In some or all embodiments of the present invention, $R^{41}$ is a $C_3$-$C_{11}$ alkyl group, such as a $C_3$-$C_7$ alkyl group, for example n-butyl, isobutyl, tert-butyl, n-pentyl, n-hexyl, n-heptyl or n-octyl alkyl group.

In the present invention, $R^{41}$ may be a straight chain $C_1$-$C_{11}$ alkyl group or a branched chain $C_3$-$C_{11}$ alkyl group.

In some or all embodiments of the present invention, $R^{41}$ is a straight chain alkyl group and the aldehyde of Formula I is selected from n-butanal, n-hexanal and n-octanal.

Advantageously, Applicant has found that the use of aldehydes of Formula I in which $R^{41}$ is a $C_3$-$C_{11}$ branched chain alkyl group or an optionally substituted aromatic group can lead to improved stability of the catalyst compared to the use of corresponding $C_3$-$C_{11}$ straight chain aldehydes.

In some or all embodiments of the present invention, $R^{41}$ is a branched chain $C_3$-$C_7$ alkyl group and suitably the aldehyde of Formula I is selected from iso-butanal and 2-ethyl hexanal.

In some or all embodiments of the present invention, in the aldehyde of Formula I, $R^{41}$ is a $C_3$-$C_7$ alkyl group in which 3 or more carbon atoms are joined to form a ring. Suitably, 4 to 7 carbon atoms may be joined to form a ring, such as 4 to 6 carbon atoms. Non-limiting examples of such aldehyde compounds are cyclopentanecarboxaldehyde, cyclohexanecarboxaldehyde and cycloheptanecarboxaldehyde.

In some or all embodiments, $R^{41}$ is an optionally substituted aromatic group, wherein the optional substituents may be independently selected from halide, a substituted or unsubstituted hydrocarbyl substituent, or a compound of the formula —CHO, —$CO_2R$, —COR, or —OR, where R is hydrogen or a substituted or unsubstituted hydrocarbyl substituent. In the embodiments where $R^{41}$ is a substituted aromatic group, the aromatic ring may comprise one or more substituents on any of meta-, ortho-, or para-positions on the aromatic ring; preferably, where $R^{41}$ is a substituted aromatic group, the aromatic ring is a para-substituted aromatic ring.

In some or all of the embodiments where $R^{41}$ is a substituted aromatic group, the substituent is a substituted or unsubstituted hydrocarbyl substituent comprising from 1 to 11 carbon atoms, preferably 1 to 9 carbon atoms, more preferably 1 to 7 carbon atoms, for example 1 to 6 carbon atoms.

By the term unsubstituted hydrocarbyl as used herein, it is meant a hydrocarbyl component which comprises from 1 to 11 carbon atoms, preferably 1 to 9 carbon atoms, more preferably 1 to 7 carbon atoms, for example 1 to 6 carbon atoms. The hydrocarbyl substituent is preferably a $C_1$-$C_{11}$ alkyl group, or a $C_3$-$C_{11}$ alkyl group in which 3 or more carbon atoms are joined to form a ring. In some or all embodiments, the hydrocarbyl substituent is a $C_1$-$C_7$ alkyl group, or a $C_3$-$C_7$ alkyl group in which 3 or more carbon atoms are joined to form a ring. In some or all embodiments, the hydrocarbyl substituent is a $C_3$-$C_{11}$ alkyl group, such as a $C_3$-$C_7$ alkyl group, for example n-butyl, isobutyl, tert-butyl, n-pentyl, n-hexyl, n-heptyl or n-octyl alkyl group.

By the term substituted hydrocarbyl as used herein, it is meant a hydrocarbyl component as described above, which comprises one or more heteroatoms. The one or more heteroatoms may conveniently be independently selected from nitrogen, oxygen, or a halide.

Acetal derivatives of the aldehydes of Formula I also function as promoters in the present invention. In the present invention, the term 'acetal derivative' also includes the hemi-acetal derivatives of the aldehydes of Formula I. As would be readily understood by a person skilled in the art, an acetal is a functional group derived from an aldehyde by replacement of the carbonyl group of the aldehyde by two alkoxy groups. A hemi-acetal is derived from an aldehyde by replacement of the carbonyl group of the aldehyde by an alkoxy group and a hydroxyl group. Consequently, the acetal derivatives of the aldehydes of Formula I may be represented by the general structural formula:

(Formula Ia)

wherein $R^{41}$ has the meaning ascribed above in Formula I and each of $R^{42}$ and $R^{43}$ is an alkyl group or hydrogen with the proviso that $R^{42}$ and $R^{43}$ are not both hydrogen.

Suitably, each of $R^{42}$ and $R^{43}$ is an alkyl group which alkyl group is a $C_1$ to $C_6$ straight or branched chain alkyl group. In these instances, $R^{42}$ and $R^{43}$ may be identical or different.

In some or all embodiments of the present invention, $R^{42}$ and $R^{43}$ are each selected from a $C_1$ or $C_2$ alkyl group. In these embodiments $R^{42}$ and $R^{43}$ may be identical or different.

In some or all embodiments of the present invention, $R^{42}$ and $R^{43}$ are identical and each is a $C_1$ alkyl group. In this instance, the acetal derivative of Formula IA is a dimethoxyacetal. Specific non-limiting examples of dimethoxy acetals are dimethoxymethane, 1,1-dimethoxyethane and 1,1-dimethoxyheptane.

In some or all embodiments of the present invention, the acetal derivative of the aldehyde of Formula I is a hemiacetal. Suitably, in these embodiments one of $R^{A2}$ and $R^{A3}$ is hydrogen and one of $R^{A2}$ and $R^{A3}$ is a $C_1$ to $C_6$ alkyl group, for example a $C_1$ to $C_3$ alkyl group. Suitably, the hemi-acetal is a methoxy hemi-acetal.

In some or all embodiments of the present invention, the aldehyde of Formula I is a cyclic aldehyde which cyclic aldehyde has 4 to 8 carbon atoms, for example 4 to 6 carbon atoms. Suitably, in these embodiments $R^{A2}$ and $R^{A3}$ of the acetal derivative of the cyclic aldehyde are each a $C_1$ to $C_2$ alkyl group and may be identical or different. Suitably, in these embodiments, $R^{A2}$ and $R^{A3}$ are identical and may be a $C_1$ alkyl group.

Aldehydes of Formula I and their acetal derivatives are available commercially.

In the present invention, a promoter of compound (i) or (ii) may be added as a component of the feed to the dehydration process. Alternatively and/or additionally, a promoter of compound (i) or (ii) may be generated in-situ by the addition to the process of any compound (a precursor compound) from which an aldehyde of Formula I or an acetal derivative thereof can be generated in-situ.

Suitable precursor compounds for the aldehyde compounds of Formula I include the acetal derivatives thereof.

The aldehyde compounds of Formula I may also be generated in-situ via retro aldol-type condensation reactions of β-hydroxyaldehyde compounds or a compound resulting from loss of water therefrom. For example, where it is desired to generate the promoter compound, acetaldehyde in-situ in the dehydration process, a suitable precursor compound which may added to the process may be butenal or the β-hydroxyaldehyde, 3-hydroxybutanal.

In some or all embodiments of the present invention, a precursor of promoter compound (i) is a β-hydroxyaldehyde compound or a compound resulting from loss of water therefrom.

Promoter compounds for use in the present invention may also be selected from (iii) ketones of Formula II, $R^{K1}COR^{K2}$, wherein $R^{K1}$ and $R^{K2}$ are identical or different and each is a $C_1$-$C_{11}$ alkyl group, a $C_3$-$C_{11}$ alkyl group in which 3 or more carbon atoms are joined to form a ring, or an optionally substituted aromatic group, and furthermore $R^{K1}$ and $R^{K2}$ together with the carbonyl carbon atom to which they are bonded may form a cyclic ketone, and (iv) ketal derivatives of ketones of Formula II.

Mixtures of ketones of Formula II and their ketal derivatives may also be used in the present invention.

In the present invention, a ketone of Formula II may be a straight alkyl chain ketone, a branched alkyl chain ketone, an aromatic ketone, or a cyclic ketone.

Advantageously, Applicant has found that the use of ketones of Formula II in which at least one of $R^{K1}$ and $R^{K2}$ is a branched chain alkyl group or an optionally substituted aromatic group can lead to improved stability of the catalyst compared to the use of corresponding straight chain ketone.

In some or all embodiments of the present invention, each of $R^{K1}$ and $R^{K2}$ may independently be a $C_1$-$C_7$ alkyl group, a $C_3$-$C_7$ alkyl group in which 3 or more carbon atoms are joined to form a ring, or an optionally substituted aromatic group.

In some or all embodiments of the present invention, each of $R^{K1}$ and $R^{K2}$ may independently be a $C_3$-$C_{11}$ alkyl group, such as a $C_3$-$C_7$ alkyl group, for example n-butyl, isobutyl, tert-butyl, n-pentyl, n-hexyl, n-heptyl or n-octyl alkyl group.

In the present invention, each of $R^{K1}$ and $R^{K2}$ may independently be a straight chain $C_1$-$C_{11}$ alkyl group or a branched chain $C_3$-$C_{11}$ alkyl group.

In some or all embodiments of the present invention, in the ketone of Formula II, each of $R^{K1}$ and $R^{K2}$ may independently be a $C_3$-$C_7$ alkyl group in which 3 or more carbon atoms are joined to form a ring. Suitably, 4 to 7 carbon atoms may be joined to form a ring, such as 4 to 6 carbon atoms.

In some or all embodiments, each of $R^{K1}$ and $R^{K2}$ may independently be an optionally substituted aromatic group, wherein the optional substituents may be independently selected from halide, a substituted or unsubstituted hydrocarbyl substituent, or a compound of the formula —CHO, —$CO_2R$, —COR, or —OR, where R is hydrogen or a substituted or unsubstituted hydrocarbyl substituent. In the embodiments where either or both of $R^{K1}$ and $R^{K2}$ is a substituted aromatic group, the aromatic ring may comprise one or more substituents on any of meta-, ortho-, or para-positions on the aromatic ring; preferably, where either or both of $R^{K1}$ and $R^{K2}$ is a substituted aromatic group, the aromatic ring is a para-substituted aromatic ring.

In some or all of the embodiments where either or both of $R^{K1}$ and $R^{K2}$ is a substituted aromatic group, the substituent is a substituted or unsubstituted hydrocarbyl substituent comprising from 1 to 11 carbon atoms, preferably 1 to 9 carbon atoms, more preferably 1 to 7 carbon atoms, for example 1 to 6 carbon atoms.

By the term unsubstituted hydrocarbyl as used herein, it is meant a hydrocarbyl component which comprises from 1 to 11 carbon atoms, preferably 1 to 9 carbon atoms, more preferably 1 to 7 carbon atoms, for example 1 to 6 carbon atoms. The hydrocarbyl substituent is preferably a $C_1$-$C_{11}$ alkyl group, or a $C_3$-$C_{11}$ alkyl group in which 3 or more carbon atoms are joined to form a ring. In some or all embodiments, the hydrocarbyl substituent is a $C_1$-$C_7$ alkyl group, or a $C_3$-$C_7$ alkyl group in which 3 or more carbon atoms are joined to form a ring. In some or all embodiments, the hydrocarbyl substituent is a $C_3$-$C_{11}$ alkyl group, such as a $C_3$-$C_7$ alkyl group, for example n-butyl, isobutyl, tert-butyl, n-pentyl, n-hexyl, n-heptyl or n-octyl alkyl group.

By the term substituted hydrocarbyl as used herein, it is meant a hydrocarbyl component as described above, which comprises one or more heteroatoms. The one or more heteroatoms may conveniently be independently selected from nitrogen, oxygen, or a halide.

In some or all embodiments of the present invention, $R^{K1}$ and $R^{K2}$ are identical or different and each is a branched chain $C_3$-$C_{11}$ alkyl group, preferably a branched chain $C_3$-$C_7$ alkyl group.

In some or all embodiments of the present invention, $R^{K1}$ and $R^{K2}$ are identical or different and each is a $C_1$-$C_3$ alkyl group.

In some or all embodiments of the present invention, one or both of $R^{K1}$ and $R^{K2}$ is a $C_3$ alkyl group and the $C_3$ alkyl group is a straight chain or branched chain $C_3$ alkyl group. Suitably, in these embodiments $R^{K1}$ and $R^{K2}$ are each a $C_3$ branched chain alkyl group and the ketone of Formula II is 2,4-dimethyl-3-pentanone.

In some or all embodiments of the present invention, $R^{K1}$ and $R^{K2}$ are identical and each is a $C_3$-$C_{11}$ alkyl group, preferably a $C_3$-$C_7$ alkyl group, for example n-propyl, isopropyl, n-butyl, isobutyl, tert-butyl, pentyl, hexyl or heptyl group.

Specific non-limiting examples of ketones suitable for use in the present invention wherein $R^{K1}$ and $R^{K2}$ are identical are acetone, 3-pentanone, 4-heptanone and 5-nonanone.

In some or all embodiments of the present invention, $R^{K1}$ and $R^{K2}$ are different, wherein $R^{K1}$ is a $C_1$-$C_3$ alkyl group and $R^{K2}$ is a $C_1$-$C_7$ alkyl group or an an optionally substituted aromatic group. Suitably, in these embodiments, $R^{K1}$ is a $C_1$ alkyl group and $R^{K2}$ is a $C_1$-$C_3$ alkyl group or an optionally substituted aromatic group.

Specific non-limiting examples of ketones suitable for use in the present invention wherein $R^{K1}$ and $R^{K2}$ are different are 2-butanone, 2-heptanone, 2-nonanone, and acetophenone.

In some or all embodiments of the present invention, the ketone of Formula II is a cyclic ketone and is suitably selected from cyclic ketones comprising 4 to 12 carbon atoms, for example 4 to 6 carbon atoms. Specific non-limiting examples of cyclic ketones of Formula II are cyclobutanone, cyclopentanone and cyclohexanone.

Ketal derivatives of the ketones of Formula II also function as promoters in the present invention. In the present invention, the term 'ketal derivative' also includes the hemi-ketal derivatives of the ketones of Formula II. As would be readily understood by a person skilled in the art, a ketal is a functional group derived from a ketone by replacement of the carbonyl group of the ketone by two alkoxy groups. A hemi-ketal is derived from a ketone by replacement of the carbonyl group of the ketone by an alkoxy group and a hydroxyl group. Consequently, the ketal derivatives of the ketones of Formula II may be represented by the general structural formula:

(Formula IIIK)

wherein $R^{K1}$ and $R^{K2}$ are identical or different and each is a $C_1$-$C_{11}$ alkyl group, a $C_3$-$C_{11}$ alkyl group in which 3 or more carbon atoms are joined to form a ring, or an optionally substituted aromatic group, and furthermore $R^{K1}$ and $R^{K2}$ together with the carbonyl carbon atom to which they are bonded may form a cyclic ketone and each of $R^{K3}$ and $R^{K4}$ is an alkyl group or hydrogen with the proviso that $R^{K3}$ and $R^{K4}$ are not both hydrogen.

Suitably, each of $R^{K3}$ and $R^{K4}$ is an alkyl group which alkyl group is a $C_1$ to $C_6$ straight or branched chain alkyl group. In these instances, $R^{K3}$ and $R^{K4}$ may be identical or different.

In some or all embodiments of the present invention, $R^{K3}$ and $R^{K4}$ are each selected from a $C_1$ or $C_2$ alkyl group. In these embodiments $R^{K3}$ and $R^{K4}$ may be identical or different.

In some or all embodiments of the present invention, $R^{K3}$ and $R^{K4}$ are identical and each is a $C_1$ alkyl group. In this instance the ketal of Formula IIIK is a dimethoxy ketal. Specific non-limiting examples of dimethoxy ketals are 2,2-dimethoxypropane and 2,2-dimethoxybutane.

In some or all embodiments of the present invention, the ketal derivative of the ketone of Formula II is a hemi-ketal. Suitably, in these embodiments one of $R^{K3}$ and $R^{K4}$ is hydrogen and one of $R^{K3}$ and $R^{K4}$ is a $C_1$ to $C_6$ alkyl group, for example a $C_1$ to $C_3$ alkyl group.

In some or all embodiments of the present invention, the ketone of Formula II is a cyclic ketone which cyclic ketone has 4 to 12 carbon atoms, for example 4 to 6 carbon atoms and $R^{K3}$ and $R^{K4}$ of the ketal derivative of the cyclic ketone are each a $C_1$ to $C_2$ alkyl group and may be identical or different. Suitably, in these embodiments, $R^{K3}$ and $R^{K4}$ are identical and may be a $C_1$ alkyl group.

Specific examples of ketal derivatives of cyclic ketones of Formula II include cyclohexanone dimethyl ketal.

Examples of suitable ketones of Formula II from which the ketal derivatives of Formula IIIK are derived include the following compounds: methyl ethyl ketone, diethyl ketone, methyl isopropyl ketone, 2,4-dimethyl-3-pentanone, 2-heptanone, 4-heptanone and 5-nonanone.

Mixtures of ketones of Formula II and the ketal derivatives of Formula IIIK may also be used in the present invention.

Ketones of Formula II and their ketal derivatives are available commercially.

In the present invention, a promoter of compound (iii) or (iv) may be added as a component of the feed to the dehydration process. Alternatively and/or additionally, a promoter of compound (iii) or (iv) may be generated in-situ by the addition to the process of any compound (a precursor compound) from which a ketone of Formula II or a ketal derivative thereof can be generated in-situ.

Suitable precursor compounds for the generation of the ketone compounds of Formula II include the ketal derivatives thereof.

The ketone compounds of Formula II may also be generated in-situ via retro aldol-type condensation reactions of β-hydroxyketone compounds. For example, where it is desired to generate acetone in-situ in the dehydration process, the precursor compound may be the β-hydroxyketone, 4-hydroxy-4-methyl-3-pentan-2-one.

In some or all embodiments of the present invention, a precursor of promoter compound (iii) is a β-hydroxyketone compound or a compound resulting from loss of water therefrom.

Promoter compounds for use in the present invention may further be selected from (v) an ester of formula $R^{E1}CO_2R^{E2}$ (Formula III), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group, and (vi) a di-ester of formula $R^{E1}(CO_2R^{E2})_2$ (Formula IV), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group.

Mixtures of esters of Formula III and di-esters of Formula IV may also be used in the present invention.

Advantageously, Applicant has found that the use of ketones of Formula II in which at least one of $R^{E1}$ and $R^{E2}$ is a branched chain alkyl group or an optionally substituted aromatic group can lead to improved stability of the catalyst compared to the use of corresponding straight chain ketone.

In some or all embodiments of the present invention, each of $R^{E1}$ and $R^{E2}$ may independently be a $C_1$-$C_7$ alkyl group, a $C_3$-$C_7$ alkyl group in which 3 or more carbon atoms are joined to form a ring, or an optionally substituted aromatic group.

In some or all embodiments of the present invention, each of $R^{E1}$ and $R^{E2}$ may independently be a $C_3$-$C_{11}$ alkyl group, such as a $C_3$-$C_7$ alkyl group, for example n-butyl, isobutyl, tert-butyl, n-pentyl, n-hexyl, n-heptyl or n-octyl alkyl group.

In the present invention, each of $R^{E1}$ and $R^{E2}$ may independently be a straight chain $C_1$-$C_{11}$ alkyl group or a branched chain $C_3$-$C_{11}$ alkyl group.

In some or all embodiments of the present invention, in the ester of Formula III or the di-ester of Formula IV, each of $R^{E1}$ and $R^{E2}$ may independently be a $C_3$-$C_7$ alkyl group in which 3 or more carbon atoms are joined to form a ring. Suitably, 4 to 7 carbon atoms may be joined to form a ring, such as 4 to 6 carbon atoms.

In some or all embodiments, each of $R^{E1}$ and $R^{E2}$ may independently be an optionally substituted aromatic group, wherein the optional substituents may be independently selected from halide, a substituted or unsubstituted hydrocarbyl substituent, or a compound of the formula —CHO, —CO$_2$R, —COR, or —OR, where R is hydrogen or a substituted or unsubstituted hydrocarbyl substituent. In the embodiments where either or both of $R^{E1}$ and $R^{E2}$ is a substituted aromatic group, the aromatic ring may comprise one or more substituents on any of meta-, ortho-, or para-positions on the aromatic ring; preferably, where either or both of $R^{E1}$ and $R^{E2}$ is a substituted aromatic group, the aromatic ring is a para-substituted aromatic ring.

In some or all of the embodiments where either or both of $R^{E1}$ and $R^{E2}$ is a substituted aromatic group, the substituent is a substituted or unsubstituted hydrocarbyl substituent comprising from 1 to 11 carbon atoms, preferably 1 to 9 carbon atoms, more preferably 1 to 7 carbon atoms, for example 1 to 6 carbon atoms.

By the term unsubstituted hydrocarbyl as used herein, it is meant a hydrocarbyl component which comprises from 1 to 11 carbon atoms, preferably 1 to 9 carbon atoms, more preferably 1 to 7 carbon atoms, for example 1 to 6 carbon atoms. The hydrocarbyl substituent is preferably a $C_1$-$C_{11}$ alkyl group, or a $C_3$-$C_{11}$ alkyl group in which 3 or more carbon atoms are joined to form a ring. In some or all embodiments, the hydrocarbyl substituent is a $C_1$-$C_7$ alkyl group, or a $C_3$-$C_7$ alkyl group in which 3 or more carbon atoms are joined to form a ring. In some or all embodiments, the hydrocarbyl substituent is a $C_3$-$C_{11}$ alkyl group, such as a $C_3$-$C_7$ alkyl group, for example n-butyl, isobutyl, tert-butyl, n-pentyl, n-hexyl, n-heptyl or n-octyl alkyl group.

By the term substituted hydrocarbyl as used herein, it is meant a hydrocarbyl component as described above, which comprises one or more heteroatoms. The one or more heteroatoms may conveniently be independently selected from nitrogen, oxygen, or a halide.

In some or all embodiments of the present invention, the ester of Formula III is an alkyl carboxylate ester wherein $R^{E1}$ an alkyl group having from 1 to 9 carbon atoms, such as from 2 to 7 carbon atoms, for example from 3 to 7 carbon atoms, and $R^{E2}$ is an alkyl group having from 1 to 3 carbon atoms, such as methyl or ethyl.

In some or all embodiments of the present invention, the ester of Formula III is an alkyl carboxylate ester wherein $R^{E2}$ an alkyl group having from 1 to 9 carbon atoms, such as from 2 to 7 carbon atoms, for example from 3 to 7 carbon atoms, and $R^{E1}$ is an optionally substituted aromatic group.

In some or all embodiments of the present invention, the ester of Formula III may be a straight alkyl chain carboxylate ester or a branched alkyl chain carboxylate ester.

In some or all embodiments of the present invention, the ester of Formula III is a straight alkyl chain carboxylate ester wherein $R^{E1}$ an alkyl group having from 1 to 9 carbon atoms, and $R^{E2}$ is a methyl or ethyl group.

In some or all embodiments of the present invention, the ester of Formula III is a straight alkyl chain carboxylate ester wherein $R^{E1}$ an alkyl group having from 2 to 7 carbon atoms, and $R^{E2}$ is a methyl or ethyl group.

In some or all embodiments of the present invention, the ester of Formula III is a straight alkyl chain carboxylate ester wherein $R^{E1}$ an alkyl group having from 1 to 9 carbon atoms, and $R^{E2}$ is a methyl or ethyl group.

Specific non-limiting examples of straight alkyl chain carboxylate esters of Formula III suitable for use in the present invention are methyl acetate, methyl propionate, methyl n-butyrate, methyl n-pentanoate, methyl n-hexanoate, methyl n-heptanoate, methyl n-octanoate, ethyl acetate, ethyl propionate, ethyl n-butyrate, ethyl n-pentanoate, ethyl n-hexanoate, ethyl n-heptanoate and ethyl n-octanoate.

In some or all embodiments of the present invention, the di-ester compound of Formula IV is a di-ester wherein $R^{E1}$ an alkyl group having from 1 to 9 carbon atoms, such as from 2 to 7 carbon atoms, for example from 2 to 4 carbon atoms or from 3 to 7 carbon atoms, and $R^{E2}$ is an alkyl group having from 1 to 3 carbon atoms, such as methyl or ethyl.

In some or all embodiments of the present invention, the di-ester compound of Formula IV is selected from at least one of dimethyl succinate, dimethyl glutarate and dimethyl adipate.

In the present invention, a promoter of compound (v) or (vi) may be added as a component of the feed to the dehydration process. Alternatively and/or additionally, a promoter of compound (v) or (vi) may be generated in-situ by the addition to the process of any compound (a precursor compound) from which an ester of Formula III or di-ester compound of Formula IV can be generated in-situ.

Precursor compounds which can be used for the in-situ generation of the ester promoter compounds of Formula III, include compounds of formula $R^{E1}CO_2X$, wherein X is selected from hydrogen, halogen, such as chlorine, and a —C(=O)—$R^1$ group wherein $R^1$ is hydrogen or an alkyl group.

Precursor compounds which can be used for the in-situ generation of the di-ester promoter compounds of Formula II, $R^{E1}(CO_2R^{E2})_2$, include compounds of formula $R^{E1}(CO_2X)_2$, wherein each X may be the same or different and is selected from hydrogen, halogen, such as chlorine, and a —C(=O)—$R^1$ group wherein $R^1$ is hydrogen or an alkyl group.

In the present invention the molar ratio of promoter to $C_2$+ alcohols is maintained throughout the dehydration reaction at less than 1. By the term 'molar ratio of promoter to $C_2$+ alcohols' or the like, it is meant the molar ratio the total amount of $C_2$+ alcohols present in the dehydration reaction to the total amount of promoter compounds in the dehydration reaction, i.e. (total amount of $C_2$+ alcohols):(total amount of promoter compounds).

In some or all embodiments of the present invention the molar ratio of promoter to $C_2$+ alcohols is maintained in the range 0.000001:1 to less than 0.5:1, preferably in the range of 0.00005:1 to less than 0.5:1. In some or all embodiments of the present invention, the molar ratio of promoter to $C_2$+ alcohols is maintained in the range of 0.00001:1 to less than 0.5:1, for example 0.00005:1 to 0.2:1, such as 0.0001:1 to 0.2:1. In some or all embodiments of the present invention, the molar ratio of promoter to $C_2$+ alcohols is maintained in the range of 0.01:1 to less than 0.5:1, for example 0.01:1 to 0.2:1, such as 0.02:1 to 0.2:1.

Suitably, in the present invention the total amount of promoter relative to the total amount of $C_2$+ alcohols is maintained throughout the dehydration reaction in an amount of at least 1 ppm. In some or all embodiments of the present invention, the total amount of promoter relative to the total amount of $C_2$+ alcohols is maintained throughout the dehydration reaction in an amount of at least 0.001 mol %, for example in an amount of 0.001 mol % to less than 50 mol %, such as 0.001 mol % to 20 mol %, for instance 0.005 mol % to 20 mol %. In some or all embodiments of the present invention, the total amount of promoter relative to the total amount of $C_2+$ alcohols is maintained throughout the dehydration reaction in an amount of at least 0.01 mol %, for example in an amount of 0.01 mol % to less than 50 mol %, such as 0.01 mol % to 20 mol %, for instance 0.05 to 20 mol %. In some or all embodiments of the present invention, the total amount of promoter relative to the total amount of $C_2+$ alcohols is maintained throughout the dehydration reaction in an amount of at least 1 mol %, for example in an amount of 1 mol % to less than 50 mol %, such as 1 mol % to 20 mol %, for instance 2 to 20 mol %.

Suitably, in the present invention, the dehydration process may be carried out as a standalone process. In such cases the dehydration reaction is not, for example carried out as part of a co-production process. Thus, suitably, in the present invention, the feed components to the process are one or more $C_2+$ alcohols and at least one promoter compound which is an carbonyl compound or derivatives thereof, such as at least one promoter compound selected from the promoter compounds of (i) to (vi) described above.

However, typically, the product stream of the $C_2+$ alcohol dehydration reaction will comprise the ether product(s), water, unconverted $C_2+$ alcohols, and one or more promoter compounds and/or precursors of the promoter compounds. Thus, in some or all embodiments of the present invention, one or more components of the product stream of the dehydration process are recycled as feed to the process. In such instances one or both of the ether products and water are additional feed components to the dehydration process.

Thus, in some or all embodiments of the present invention the feed components to the dehydration process are $C_2+$ alcohols, at least one promoter compound which is an carbonyl compound or derivatives thereof, such as at least one promoter compound selected from the promoter compounds of (i) to (vi) described above, and one or both of the ether products and water.

In instances where it is desired to generate the promoter in situ in the dehydration process the feed components to the process may be at least one $C_2+$ alcohol and at least one precursor compound of the promoter or promoters.

Thus, in some or all embodiments of the present invention the feed components to the dehydration process are the $C_2+$ alcohols, one or both of (i) a promoter compound as described herein, and (ii) at least one precursor compound of a promoter compound as described herein; and one or both of the ether products and water.

The feed components to the process may be supplied to the process in one or more feed streams.

The dehydration process is carried out as a heterogeneous process, either as a vapour phase heterogeneous process or as a liquid phase heterogeneous process.

The type of reactor used for the dehydration process is not limited, and it may be suitably carried out in any type of reactor within which a vapour phase heterogeneous process or a liquid phase heterogeneous process may be performed. Non-limiting types of reactors with which the dehydration reaction may be performed include tank reactors, multi-tubular reactors, plug-flow reactors, loop reactors, fluidized bed reactors, and reactive distillation columns.

The dehydration process may be carried out at a temperature of from 100 to 300° C. In some or all embodiments of the present invention, the dehydration process is carried out at a temperature of from 140 to 250° C., for example from 150 to 250° C.

Suitably, the dehydration process may be carried out at atmospheric pressure or at elevated pressure.

In some or all embodiments of the present invention, the dehydration process is carried out at a total pressure of atmospheric pressure to 3000 kPa. Where the process is conducted in the liquid phase, higher total pressures, such as 4000 kPa to 10,000 kPa, may be required to maintain the ether product in solution.

In some or all embodiments of the present invention, the dehydration process is carried out as a heterogeneous vapour phase process at a total pressure of atmospheric pressure to 3000 kPa. In these embodiments, the temperature may be from 100 to 300° C., such as from 140 to 250° C., for example from 150 to 250° C.

For vapour phase processes, the process may be carried out at a total gas hourly space velocity (GHSV) in the range 500 to 40,000 $h^{-1}$.

For liquid phase processes, the process may be carried out at a total liquid hourly space velocity (LHSV) in the range 0.2 to 20 $h^{-1}$.

The dehydration process may be carried out using one or more beds of zeolite catalyst, suitably selected from fixed bed, fluidised bed, and moving beds of catalyst.

The dehydration process may be operated as either a continuous or a batch process, preferably as a continuous process.

The dehydration process generates a crude reaction product comprising the ether(s) and water as reaction products, unreacted $C_2+$ alcohols and one or more compounds selected from promoter compounds and promoter precursor compounds. One or more components of the crude reaction product may be recycled as feed to the process.

The ether product(s) may be recovered from the crude reaction product by any suitable method, for example by distillation methods.

Without being bound by theory, the productivity of catalysts will typically decrease over time on stream; in industrially applied catalytic processes, one of the ways by which the decrease in productivity may be compensated for is by increasing the reaction temperature to maintain a consistent productivity. A disadvantage of increasing the temperature of the reaction is that this may lead to an increase in undesirable by-products or may result in a decrease in selectivity; another disadvantage of increasing the temperature of the reaction is that such an increase in temperature may accelerate the rate of catalyst deactivation. However, without wishing to be bound by theory, it is believed that in the present invention, decreases in productivity of the catalyst may be at least in part compensated for by increasing the relative concentration of the promoter in the $C_2+$ alcohol feed, and thus may reduce or eliminate the need for an increase in temperature to compensate for any reduction in productivity which may occur with time on stream; similarly, decreases in productivity of the catalyst may be at least in part compensated for by changing the promoter used or by adding a second or further additional promoter compound to the $C_2+$ alcohol(s) feed as the time on stream increases.

In addition to the beneficial effect on the rate of dehydration of $C_2+$ alcohols reactions carried out in the presence of at least one aluminosilicate zeolite catalyst which is a medium pore zeolite having a 3-dimensional framework structure, it is believed that the use of promoters as described herein may result in an increase in the stability of the catalyst and may make the catalyst more resistant to deactivation by impurities present in the $C_2+$ alcohol feed.

In a further aspect of the present invention, there is provided a process for dehydrating $C_2+$ alcohols to ether products in the presence of a catalyst, wherein the catalyst is at least one aluminosilicate zeolite catalyst which is a medium pore zeolite having a 3-dimensional framework structure, and wherein prior to using the catalyst in the dehydration process, the catalyst has been impregnated with a promoter which is an organic carbonyl compound or derivative thereof.

In a particular embodiment of this further aspect of the present invention, there is provided a process for dehydrating $C_2+$ alcohols to ether products in the presence of a catalyst, wherein the catalyst is at least one aluminosilicate zeolite catalyst which is a medium pore zeolite having a 3-dimensional framework structure, and wherein prior to using the catalyst in the dehydration process, the catalyst has been impregnated with a promoter selected from:
(i) an aldehyde of formula $R^{A1}$CHO(Formula I), $R^{A1}$CHO, wherein $R^{A1}$ is hydrogen, a $C_1$-$C_{11}$ alkyl group, a $C_3$-$C_{11}$ alkyl group in which 3 or more carbon atoms are joined to form a ring, or an optionally substituted aromatic group;
(ii) an acetal derivative of an aldehyde of Formula I;
(iii) a ketone of formula $R^{K1}COR^{K2}$ (Formula II), wherein $R^{K1}$ and $R^{K2}$ are identical or different and each is a $C_1$-$C_{11}$ alkyl group, a $C_3$-$C_{11}$ alkyl group in which 3 or more carbon atoms are joined to form a ring, or an optionally substituted aromatic group, and furthermore $R^{K1}$ and $R^{K2}$ together with the carbonyl carbon atom to which they are bonded may form a cyclic ketone;
(iv) a ketal derivative of a ketone of Formula II;
(v) an ester of formula $R^{E1}CO_2R^{E2}$ (Formula III), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group; and,
(vi) a di-ester of formula $R^{E1}(CO_2R^{E2})_2$ (Formula IV), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group.

In this further aspect of the invention, the feed to the dehydration process comprises the $C_2+$ alcohols and may optionally comprise other components, for example ethers, water, or at least one promoter which is an organic carbonyl compound or derivative thereof, such as at least one promoter compound selected from the promoter compounds of (i) to (vi) described above, or a precursor compound thereof.

The invention is now illustrated with reference to the following non-limiting Examples.

EXAMPLES

The ZSM-5 catalysts used in Examples 1 to 11 were obtained in ammonium-form from Zeolyst International. The ZSM-11 catalyst used in Example 12 was obtained in ammonium-form from ACS Material. The ZSM-5 and ZSM-11 catalysts were utilised in their H-form after conversion by calcination in air at 500° C.

General Reaction Method and Apparatus I

The ethanol dehydration reactions were carried out using a 16-channel parallel fixed-bed stainless steel reactor system. Each reactor (2 mm internal diameter) was heated to maintain a temperature of 150 or 200° C. Each reactor housed a 25 mg bed of catalyst (having particle size fraction of 100 to 200 microns diameter) loaded on top of a 6 cm deep bed of an inert material (carborundum). The reactor volume above the catalyst was also packed with carborundum. The reactor was set-up in a down-flow configuration.

Each reactor was maintained at a temperature of 150° C. and at a total pressure of 1100 kPa throughout the reactions.

A gaseous feed comprising 10 mol % ethanol and inert gas was introduced into the reactor at a constant flow rate of ethanol of 13 mmol $h^{-1}$ and allowed to flow through the catalyst bed for a period of at least 24 hours. Different concentrations of promoters were added to the feed in order to determine the impact on the yield of diethyl ether. The flow rate of inert gas was reduced to maintain a constant gas-hourly space velocity upon addition of the promoter and the ethanol flow rate was maintained at 13 mmol $h^{-1}$.

The effluent stream from each reactor was diluted with inert gas (nitrogen) and was periodically analysed by online gas chromatography to determine the yield of diethyl ether product.

General Reaction Method and Apparatus II

The n-hexanol dehydration reactions were carried out using a single-channel fixed-bed stainless steel reactor system. The reactor housed a 350 mg bed of ZSM-5 catalyst with a silica to alumina ratio (SAR) of 80. The catalyst had a particle size fraction of 250 to 500 microns diameter. The catalyst was loaded below a 170 mg pre-bed of inert material (silicon carbide) and above a 600 mg post-bed of inert material (silicon carbide).

The reactor was maintained at a temperature of 160° C. and at a pressure of 20 barg throughout the reactions.

Example 1

This Example demonstrates the effect of ethyl formate on ethanol dehydration reactions over different ZSM-5 catalysts at a reaction temperature of 150° C.

The ethanol dehydration reactions were carried out using the General Reaction Method and Apparatus I described above at a reaction temperature of 150° C. The observed space time yields to diethyl ether product are provided in Table 1.

TABLE 1

| | | Diethyl ether STY/g $kg^{-1}$ $h^{-1}$ | | | |
|---|---|---|---|---|---|
| Catalyst | SAR | No co-feed | 5 mol % ethyl formate co-feed | 10 mol % ethyl formate co-feed | 20 mol % ethyl formate co-feed |
| ZSM-5 | 23 | 592 | 1227 | 1567 | 2072 |
| ZSM-5 | 80 | 291 | 1388 | 1839 | 2492 |
| ZSM-5 | 280 | 97 | 605 | 800 | 1076 |

SAR indicates the silica:alumina molar ratio of a zeolite

The results in Table 1 show that the use of ethyl formate enhances the space time yields to diethyl ether.

Example 2

This Example demonstrates the effect of ethyl formate on ethanol dehydration reactions over different ZSM-5 catalysts at a reaction temperature of 200° C.

The ethanol dehydration reactions were carried out using the General Reaction Method and Apparatus I described above at a reaction temperature of 200° C. The observed space time yields to diethyl ether product are provided in Table 2.

TABLE 2

| | | Diethyl ether STY/g kg$^{-1}$ h$^{-1}$ | |
|---|---|---|---|
| Catalyst | SAR | No co-feed | 10 mol % ethyl formate co-feed |
| ZSM-5 | 23 | 11851 | 15200 |
| ZSM-5 | 80 | 8605 | 17274 |
| ZSM-5 | 280 | 1634 | 7603 |

SAR indicates the silica:alumina molar ratio of a zeolite

The results in Table 2 show that the use of ethyl formate enhances the space time yields to diethyl ether.

Example 3

This Example demonstrates the effect of ethyl n-butyrate on ethanol dehydration reactions over different ZSM-5 catalysts.

The ethanol dehydration reactions were carried out using the General Reaction Method and Apparatus I described above at a reaction temperature of 150° C. The observed space time yields to diethyl ether product are provided in Table 3.

TABLE 3

| | | Diethyl ether STY/g kg$^{-1}$ h$^{-1}$ | | | | |
|---|---|---|---|---|---|---|
| | | | ethyl n-butyrate co-feed | | | |
| Catalyst | SAR | No co-feed | 0.1 mol % | 1 mol % | 5 mol % | 10 mol % | 20 mol % |
| ZSM-5 | 23 | 504 | 510 | 554 | 666 | 766 | 1006 |
| ZSM-5 | 80 | 317 | 337 | 469 | 940 | 1384 | 1904 |
| ZSM-5 | 280 | 77 | 82 | 120 | 256 | 347 | 476 |

SAR indicates the silica: alumina molar ratio of a zeolite

The results in Table 3 show that the use of ethyl n-butyrate enhances the space time yields to diethyl ether.

Example 4

This Example demonstrates the effect of dimethyl adipate on ethanol dehydration reactions over different ZSM-5 catalysts.

The ethanol dehydration reactions were carried out using the General Reaction Method and Apparatus I described above at a reaction temperature of 150° C. The observed space time yields to diethyl ether product are provided in Table 4.

TABLE 4

| | | Diethyl ether STY/g kg$^{-1}$ h$^{-1}$ | |
|---|---|---|---|
| Catalyst | SAR | No co-feed | 0.01 mol % dimethyl adipate co-feed |
| ZSM-5 | 23 | 499 | 596 |
| ZSM-5 | 80 | 356 | 577 |
| ZSM-5 | 280 | 79 | 159 |

SAR indicates the silica:alumina molar ratio of a zeolite

The results in Table 4 show that the use of dimethyl adipate enhances the space time yields to diethyl ether.

Example 5

This Example demonstrates the effect of 5-nonanone on ethanol dehydration reactions over different ZSM-5 catalysts.

The ethanol dehydration reactions were carried out using the General Reaction Method and Apparatus I described above at a reaction temperature of 150° C. The observed space time yields to diethyl ether product are provided in Table 5.

TABLE 5

| | | Diethyl ether STY/g kg$^{-1}$ h$^{-1}$ | |
|---|---|---|---|
| Catalyst | SAR | No co-feed | 0.01 mol % 5-nonanone |
| ZSM-5 | 23 | 617 | 654 |
| ZSM-5 | 80 | 299 | 420 |
| ZSM-5 | 280 | 77 | 209 |

SAR indicates the silica:alumina molar ratio of a zeolite

The results in Table 5 show that the use of 5-nonanone enhances the space time yields to diethyl ether.

Example 6

This Example demonstrates the effect of acetone on ethanol dehydration reactions over different ZSM-5 catalysts.

The ethanol dehydration reactions were carried out using the General Reaction Method and Apparatus I described above at a reaction temperature of 150° C. The observed space time yields to diethyl ether product are provided in Table 6.

TABLE 6

| | | Diethyl ether STY/g kg$^{-1}$ h$^{-1}$ | |
|---|---|---|---|
| Catalyst | SAR | No co-feed | 0.01 mol % acetone |
| ZSM-5 | 23 | 597 | 601 |
| ZSM-5 | 80 | 284 | 296 |
| ZSM-5 | 280 | 72 | 75 |

SAR indicates the silica:alumina molar ratio of a zeolite

The results in Table 6 show that the use of acetone enhances the space time yields to diethyl ether.

Example 7

This Example demonstrates the effect of 1,1-diethoxyethane on ethanol dehydration reactions over different ZSM-5 catalysts.

The ethanol dehydration reactions were carried out using the General Reaction Method and Apparatus I described above at a reaction temperature of 150° C. The observed space time yields to diethyl ether product are provided in Table 7.

TABLE 7

| | | Dietliyl ether STY/g kg$^{-1}$ h$^{-1}$ | |
|---|---|---|---|
| Catalyst | SAR | No co-feed | 0.05 mol % 1,1-diethoxyethane |
| ZSM-5 | 23 | 592 | 648 |
| ZSM-5 | 80 | 275 | 382 |
| ZSM-5 | 280 | 67 | 98 |

SAR indicates the silica:alumina molar ratio of a zeolite

The results in Table 7 show that the use of 1,1-diethoxyethane enhances the space time yields to diethyl ether.

Example 8

This Example demonstrates the effect of benzaldehyde on ethanol dehydration reactions over different ZSM-5 catalysts.

The ethanol dehydration reactions were carried out using the General Reaction Method and Apparatus I described above at a reaction temperature of 150° C. The observed space time yields to diethyl ether product are provided in Table 8.

TABLE 8

| | | Diethyl ether STY/g kg$^{-1}$ h$^{-1}$ | | |
|---|---|---|---|---|
| Catalyst | SAR | No co-feed | 0.01 mol % benzaldehyde | 0.1 mol % benzaldehyde |
| ZSM-5 | 23 | 573 | 604 | 903 |
| ZSM-5 | 80 | 287 | 616 | 1836 |
| ZSM-5 | 280 | 90 | 182 | 598 |

SAR indicates the silica:alumina molar ratio of a zeolite

The results in Table 8 show that the use of benzaldehyde enhances the space time yields to diethyl ether.

Example 9

This Example demonstrates the effect of n-butanal on ethanol dehydration reactions over different ZSM-5 catalysts.

The ethanol dehydration reactions were carried out using the General Reaction Method and Apparatus I described above at a reaction temperature of 150° C. The observed space time yields to diethyl ether product are provided in Table 9.

TABLE 9

| | | Diethyl ether STY/g kg$^{-1}$ h$^{-1}$ | | |
|---|---|---|---|---|
| Catalyst | SAR | No co-feed | 0.01 mol % n-butanal | 0.1 mol % n-butanal |
| ZSM-5 | 23 | 544 | 558 | 567 |
| ZSM-5 | 80 | 281 | 309 | 423 |
| ZSM-5 | 280 | 73 | 88 | 140 |

SAR indicates the silica:alumina molar ratio of a zeolite

The results in Table 9 show that the use of n-butanal enhances the space time yields to diethyl ether.

Example 10

This Example demonstrates the effect of benzaldehyde on n-hexanol dehydration reactions over a ZSM-5 catalyst.

The n-hexanol dehydration reactions were carried out using the General Reaction Method and Apparatus II described above. A liquid feed was introduced into the reactor at a constant flow rate of 0.08 ml min$^{-1}$ to achieve a liquid hourly space velocity (LHSV) of 10 mL mL$_{cat}^{-1}$ h$^{-1}$. The reactor was set-up in a down-flow configuration. A liquid sample was analysed by an off-line gas chromatography (GC) at 3.5 h time on stream (ToS).

At 3.5 h ToS the liquid feed was changed to one consisting of 1 mol % benzaldehyde (1.06 g) in n-hexanol (101.14 g); all other variables remained the same. At 5.5 h ToS a liquid sample was analysed by off-line GC. The observed space time yields to dihexyl ether and hexene products are provided in Table 10.

TABLE 10

| | STY/g kg$^{-1}$ h$^{-1}$ | |
|---|---|---|
| Product | No co-feed (ToS = 3.5 h) | 1 mol % benzaldehyde co-feed (ToS = 5.5 h) |
| Hexene | 86 | 73 |
| Dihexyl ether | 287 | 360 |

The results in Table 10 show that the use of benzaldehyde enhances the space time yield to dihexyl ether.

Example 11

This Example demonstrates the effect of 4-trifluorobenzaldehyde on n-hexanol dehydration reactions over a ZSM-5 catalyst.

The n-hexanol dehydration reactions were carried out using the General Reaction Method and Apparatus II described above. A liquid feed was introduced into the reactor at a constant flow rate of 0.08 ml min$^{-1}$ to achieve a liquid hourly space velocity (LHSV) of 10 mL mL$_{cat}^{-1}$ h$^{-1}$. The reactor was set-up in a down-flow configuration. A liquid sample was analysed by an off-line gas chromatography (GC) at 4.25 h time on stream (ToS).

At 4.25 h ToS the liquid feed was changed to one consisting of 1 mol % 4-fluorobenzaldehyde (1.746 g) in n-hexanol (101.14 g); all other variables remained the same. At 6.25 h ToS a liquid sample was analysed by off-line GC. The observed space time yields to dihexyl ether and hexene products are provided in Table 11.

TABLE 11

| | STY/g kg$^{-1}$ h$^{-1}$ | |
|---|---|---|
| Product | No co-feed (ToS = 4.25 h) | 1 mol % 4-trifluorobenzaldehyde co-feed (ToS = 6.25 h) |
| Hexene | 58 | 44 |
| Dihexyl ether | 287 | 312 |

The results in Table 11 show that the use of 4-trifluorobenzaldehyde enhances the space time yield to dihexyl ether.

Example 12

This Example demonstrates the effect of ethyl formate on ethanol dehydration reactions over ZSM-5 and ZSM-11 catalysts at a reaction temperature of 150° C.

The ethanol dehydration reactions were carried out using the General Reaction Method and Apparatus I described above at a reaction temperature of 150° C. The observed space time yields to diethyl ether product are provided in Table 12.

TABLE 12

| | | Diethyl ether STY/g kg$^{-1}$ h$^{-1}$ | |
|---|---|---|---|
| Catalyst | SAR | No co-feed | 5 mol % ethyl formate co-feed |
| ZSM-5 | 50 | 376 | 1435 |
| ZSM-11 | 50 | 372 | 1381 |

SAR indicates the silica:alumina molar ratio of a zeolite

The results in Table 12 show that the use of ethyl formate enhances the space time yields to diethyl ether.

The invention claimed is:

1. A process comprising dehydrating $C_2$+ alcohols to ether products in the presence of a catalyst and promoter, wherein the catalyst is at least one aluminosilicate zeolite catalyst which is a medium pore zeolite having a 3-dimensional framework structure, and the promoter is one or more organic carbonyl compounds or derivatives thereof, and wherein and the molar ratio of promoter to $C_2$+ alcohols is maintained at less than 1.

2. A process according to claim 1, wherein the promoter is one or more compounds selected from:
   (i) an aldehyde of formula $R^{A1}CHO$ (Formula I), wherein $R^{A1}$ is hydrogen, a $C_1$-$C_{11}$ alkyl group, a $C_3$-$C_{11}$ alkyl group in which 3 or more carbon atoms are joined to form a ring, or an optionally substituted aromatic group;
   (ii) an acetal derivative of an aldehyde of Formula I;
   (iii) a ketone of formula $R^{K1}COR^{K2}$ (Formula II), wherein $R^{K1}$ and $R^{K2}$ are identical or different and each is a alkyl group, a $C_1$-$C_{11}$ alkyl group, a $C_3$-$C_{11}$ in which 3 or more carbon atoms are joined to form a ring, or an optionally substituted aromatic group, and furthermore $R^{K1}$ and $R^{K2}$ together with the carbonyl carbon atom to which they are bonded may form a cyclic ketone;
   (iv) a ketal derivative of a ketone of Formula II;
   (v) an ester of formula $R^{E1}CO_2R^{E2}$ (Formula III), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group; and
   (vi) a di-ester of formula $R^{E1}(CO_2R^{E2})_2$ (Formula IV), wherein $R^{E1}$ and $R^{E2}$ are identical or different and are each a $C_1$-$C_{11}$ alkyl group, a $C_3$-$C_{11}$ alkyl group in which 3 or more carbon atoms are joined to form a ring, or an optionally substituted aromatic group.

3. A process according to claim 1, wherein the aluminosilicate zeolite catalyst is a medium pore zeolite having a 3-dimensional framework structure.

4. A process according to claim 3, wherein the aluminosilicate zeolite catalyst is selected from framework types MFI and MEL.

5. A process according to claim 4, wherein the aluminosilicate zeolite catalyst is selected from ZSM-5 or ZSM-11.

6. A process according to claim 1, wherein the aluminosilicate zeolite is composited with a binder material.

7. A process according to claim 1, wherein the $C_2$+ alcohols to be dehydrated are primary alcohols comprising a $C_2$ to $C_6$ alkyl group and a hydroxyl group.

8. A process according to claim 1, wherein the $C_2$+ alcohols to be dehydrated is one or more alcohols selected from the group comprising ethanol, n-propanol, and n-butanol.

9. A process according to claim 1, wherein the $C_2$+ alcohols to be dehydrated is a single $C_2$+ alcohol species.

10. A process according to claim 1, wherein the molar ratio of promoter to $C_2$+ alcohol is maintained in the range 0.00001:1 to 0.2:1.

11. A process according to claim 1, wherein the promoter is generated in-situ in the dehydration process.

12. A process according to claim 1, wherein the process is carried out at a temperature of from 100° C. to 300° C.

13. A process according to claim 1, wherein the process is carried out as a heterogeneous vapour phase process.

14. A method of improving the productivity to ether products in a process for dehydrating $C_2$+ alcohols, the method comprising dehydrating $C_2$+ alcohols to ether products in the presence of a catalyst and a promoter, wherein the catalyst is at least one aluminosilicate zeolite catalyst which is a medium pore zeolite having a 3-dimensional framework structure, and the promoter is one or more organic carbonyl compounds or derivatives thereof, and wherein and the molar ratio of promoter to $C_2$+ alcohols is maintained at less than 1.

15. A process comprising dehydrating $C_2$+ alcohols to ether products in the presence of a catalyst, wherein the catalyst is at least one aluminosilicate zeolite catalyst which is a medium pore zeolite having a 3-dimensional framework structure, and wherein prior to using the catalyst in the dehydration process, the catalyst has been impregnated with a promoter which is an organic carbonyl compound or derivative thereof.

* * * * *